United States Patent
Kopacko et al.

(10) Patent No.: US 7,665,464 B2
(45) Date of Patent: Feb. 23, 2010

(54) RESPIRATORY MASK

(75) Inventors: Ralph E Kopacko, Irwin, PA (US);
Zachary D Paul, Pittsburgh, PA (US);
Shari S Barnett, Cardiff, CA (US)

(73) Assignee: Ric Investments, LLC, Wilmington, DE (US)

( * ) Notice: Subject to any disclaimer, the term of this patent is extended or adjusted under 35 U.S.C. 154(b) by 72 days.

(21) Appl. No.: 10/251,490

(22) Filed: Sep. 20, 2002

(65) Prior Publication Data

US 2003/0019496 A1  Jan. 30, 2003

Related U.S. Application Data

(63) Continuation of application No. 09/362,402, filed on Jul. 28, 1999, now Pat. No. 6,467,483.

(51) Int. Cl.
*A62B 18/08* (2006.01)
(52) U.S. Cl. .................. 128/206.24; 128/202.27; 128/205.25; 128/205.29; 128/206.12; 128/206.13; 128/206.21; 128/206.28; 128/206.29; 128/206.27; 128/207.11; 128/207.12; 128/207.13; 128/912
(58) Field of Classification Search ............ 128/202.27, 128/205.25, 205.29, 206.12, 206.13, 206.21, 128/206.24, 206.28, 206.29, 206.27, 207.11, 128/207.12, 207.13, 912
See application file for complete search history.

(56) References Cited

U.S. PATENT DOCUMENTS

| | | | | |
|---|---|---|---|---|
| 417,795 A * | 12/1889 | Starr | ...................... | 128/205.25 |
| 2,837,090 A * | 6/1958 | Bloom et al. | .......... | 128/206.24 |
| 4,167,185 A * | 9/1979 | Lewis | .................... | 128/206.24 |
| 4,655,213 A | 4/1987 | Rapoport et al. | | |
| 4,677,977 A | 7/1987 | Wilcox | | |
| 4,739,755 A | 4/1988 | White et al. | | |
| 4,907,584 A | 3/1990 | McGinnis | | |
| 4,944,310 A | 7/1990 | Sullivan | | |
| 4,971,051 A | 11/1990 | Toffolon | | |
| 5,243,971 A * | 9/1993 | Sullivan et al. | ........ | 128/205.25 |
| 5,349,949 A | 9/1994 | Schegerin | | |
| 5,492,116 A | 2/1996 | Scarberry et al. | | |

(Continued)

FOREIGN PATENT DOCUMENTS

WO    WO95/32023    * 11/1995    ............ 128/205.25

OTHER PUBLICATIONS

Sales Brochure—"Comfort Flap Mask Accessory", Respironics, Inc. 1994.

(Continued)

*Primary Examiner*—Patricia Bianco
*Assistant Examiner*—Nihir Patel
(74) *Attorney, Agent, or Firm*—Michael W. Haas

(57) ABSTRACT

A respiratory mask having a flexible, mask seal portion for engagement with the face of a user, a gel forehead cushion and a rotatable elbow coupling having integral exhaust ports. The mask seal portion has a thin section which permits the mask to more easily adapt to the contour of the face of the user. The gel forehead cushion provides increased compliancy and resiliency to better adapt to multiple user physical profiles. The elbow coupling includes tapered through holes in a polycarbonate arc piece to provide a quiet passage of gas through the holes.

19 Claims, 9 Drawing Sheets

U.S. PATENT DOCUMENTS

| | | | |
|---|---|---|---|
| 5,517,986 A | | 5/1996 | Starr et al. |
| 5,540,223 A | | 7/1996 | Starr et al. |
| 5,560,354 A | | 10/1996 | Berthon-Jones et al. |
| 5,570,689 A | * | 11/1996 | Starr et al. ............. 128/207.11 |
| 5,647,357 A | * | 7/1997 | Barnett et al. .......... 128/206.24 |
| 5,724,965 A | | 3/1998 | Handke et al. |
| 5,746,201 A | | 5/1998 | Kidd |
| 5,884,624 A | * | 3/1999 | Barnet et al. ........... 128/206.24 |
| 5,921,239 A | * | 7/1999 | McCall et al. ......... 128/205.25 |
| 5,944,013 A | * | 8/1999 | Burch ................... 128/205.14 |
| 5,966,745 A | * | 10/1999 | Schwartz et al. ................ 2/428 |
| 6,006,748 A | * | 12/1999 | Hollis ................... 128/205.24 |
| 6,039,044 A | * | 3/2000 | Sullivan ................ 128/205.25 |
| 6,098,205 A | * | 8/2000 | Schwartz et al. ................ 2/428 |
| 6,112,746 A | * | 9/2000 | Kwok et al. ........... 128/207.13 |
| 6,119,693 A | * | 9/2000 | Kwok et al. ........... 128/207.11 |
| 6,152,137 A | * | 11/2000 | Schwartz et al. ............ 128/846 |
| 6,397,847 B1 | * | 6/2002 | Scarberry et al. ...... 128/206.24 |
| 6,467,483 B1 | * | 10/2002 | Kopacko et al. ....... 128/207.12 |

OTHER PUBLICATIONS

Sales Brochure—"Spectrum Reusable Full Face Mask", Respironics, Inc. 1998.
Sales Brochure—"Small Child Reusable Nasal Mask", Respironics, Inc. 1994.
Sales Brochure—"Monarch Ultra Mini Mask", Respironics, Inc. 1998.
Sales Brochure—"The Softest, Silkiest CPAP Mask Available", Respironics, Inc. 1998.
United States Statutory Invention Registration, "Modified Bubble Inturn Mask Periphery", H397, Stark, Jan. 5, 1998.

* cited by examiner

RESPIRATORY MASK

CROSS REFERENCE TO RELATED APPLICATIONS

This application claims priority under 35 U.S.C. § 120 as a Continuation of U.S. patent application Ser. No. 09/362,402 filed Jul. 28, 1999 now U.S. Pat. No. 6,467,483.

BACKGROUND OF THE INVENTION

1. Field of the Invention

The present invention relates, in general, to respiratory masks and mask couplings and, more particularly, to respiratory masks having flexible seals adapted to receive portions of a patient's face for preventing leakage of gas supplied to the patient, forehead cushions for use with such masks, and conduit couplings having an exhaust port to exhaust $CO_2$ laden air.

2. Description of the Related Art

A variety of respiratory masks are known that have flexible seals and cover the nose, mouth, or both of a human user and are designed to create a continuous seal against the user's face. Because of the sealing effect that is created, gases can be provided at a positive pressure within the mask for consumption by the user. The uses for such masks range from high altitude breathing (i.e., aviation applications) to mining and fire fighting applications, to various medical diagnostic and therapeutic applications, including the treatment of obstructive sleep apnea with positive airway pressure devices.

One requisite of such respiratory masks has been that they provide an effective seal against the user's face to prevent the gas being supplied from leaking at the mask-to-face interface. Commonly, in prior mask configurations, a good mask-to-face seal has been attained in many instances only with considerable discomfort for the user. This problem is most crucial in those applications, especially medical applications, that require the user to wear such a mask continuously for an extended periods of time, such as hours or perhaps even days. In such situations, the user may not tolerate wearing the mask for long durations, and, as a result, optimum therapeutic or diagnostic objectives will not be achieved, or will be achieved with great difficulty and considerable user discomfort.

At least two types of respiratory face masks are known for the types of applications mentioned above. The most common type of mask incorporates a smooth sealing surface extending around the periphery of the mask and exhibiting a generally uniform (i.e., predetermined or fixed) seal surface contour that is intended to be effective to seal against the user's face when force is applied to the mask, with the smooth sealing surface in confronting engagement with the user's face. The sealing surface may consist of an air or fluid filled cushion, or it may simply be a molded or formed surface of a resilient seal element made of an elastomer, such as plastic or rubber.

Such masks have performed well when the fit is good between the contours of the seal surface and the corresponding contours of the user's face. However, if the seal fit is not good, there will be gaps in the seal-to-face interface, and excessive force will be required to compress the seal member to attain a satisfactory seal in those areas where gaps occur. Such excessive force is unacceptable, as it produces high pressure points elsewhere on the face of the user where the mask seal contour is forcibly deformed against the face to conform to the user's facial contours. This will produce considerable user discomfort anywhere the applied force exceeds the local perfusion pressure, which is the pressure that is sufficient to cut off surface blood flow. Ideally, contact forces should be limited between the mask and the user's face to avoid exceeding the local perfusion pressure even at points where the mask seal must deform considerably.

The problem of seal contact force exceeding desirable limits is even more pronounced when the positive pressure of the gas being supplied is relatively high or is cyclical to high levels. Because the mask seals by virtue of confronting contact between the mask seal and the user's face, the mask must be held against the face with a force sufficient to seal against leakage of the peak pressure of the supplied gas. Thus, for conventional masks, when the supply pressure is high, headstraps or other mask restraints must be tightly fastened. This produces high localized pressure on the face, not only in the zone of the mask seal but at various locations along the extent of the retention straps as well. This too will result in severe discomfort for the user after only a brief period of time. Even in the absence of excessive localized pressure points, the tight mask and headstraps often may become extremely uncomfortable and user discomfort may well cause discontinued cooperation with the regimen. Examples of respiratory masks possessing continuous cushion sealing characteristics of the type just described are provided in U.S. Pat. Nos. 2,254,854 and 2,939,458.

A second type of mask, which has been used with a measure of success, incorporates a flap seal of thin material positioned about the periphery of the mask as to provide a self-sealing action against the face of the user when positive pressure is applied within the mask. In such a mask, the flap seal typically defines a contoured sealing surface adapted for confronting and sealing engagement with the user's face. Under the influence of a flow of pressurized gas supplied to the interior of the mask, which impinges upon the surface opposite the contoured sealing surface, the sealing surface is urged into sealing contact with the user's face. With this type of sealing action, the forces that serve to hold the mask in confronting engagement on the face of the user are much lower than the strapping forces associated with the first type of mask described above. If the flap seal is capable of conforming to the contours of the user's face without forming leak paths, the mask can be used with retention straps that exert little or no net force to push the mask against the user's face. Thus, the overall sensation of constraint and confinement is dramatically reduced for the user. Such a mask, when properly adjusted, can be adapted to any positive internal mask pressure. The sealing flap will be self-sealing as long as there is no looseness in the strapping arrangement which would allow the mask to move away from the face further than the reach of the sealing flap when subjected to internal pressure.

There are two potential limitations of the above described mask type having a sealing flap characteristic. First, the sealing flap seals by laying flat against the user's face throughout its length. This action requires a close match between the contours of the face and the contours of the seal. If the match is not good, the seal will be ineffective. Second, the normal response of one applying the mask to a user's face is to push the mask harder against the user's face if the mask does not seal. With the typical flap seal-type mask, increasing contact pressure against the user's face will not help to form an effective seal if the flap seal does not initially fit well to the facial contours. It may, however, lead to patient discomfort and other problems as described above.

Some of the principal problems one encounters when trying to apply the self-sealing flap concept to the design of the respiratory mask are related to the location of relative low points and high points in the facial contours of the user relative to the shape or contour of the flap seal surface. If the seal surface does not contact the user's face at the relative lower points, then excessive gas leakage will occur, thus preventing sufficient internal gas pressure to develop to activate the sealing action of the seal flap at the low points. In the past, this problem has been solved for some applications by providing a variety of masks with differing seal flap shapes, sizes and contours. For example, for aircraft breathing masks, especially where expense is not a critical factor, wide variety of mask shapes and sizes may be provided to give the individual users an opportunity to find a mask offering good fit. In other breathing mask applications, such as a clinical use, where economic considerations may dictate a mask having the capability to accommodate a wide variety of facial sizes and contours, prior flap type seal structures have not generally been able to provide the requisite versatility.

A related problem with flap seal mask structures concerns the high points of the user's face, where the seal flap may tend to distort or collapse and fold in on itself, thus creating a channel for gas leakage, when pressure is applied in order to effect a seal at adjacent relative low points on the user's face. Even where the section thickness of the seal flap is very thin, and the material is very soft and flexible, the internal gas pressure cannot overcome such seal flap distortion to provide the desired self-sealing.

A mask of the above-characterized flap seal type is described in U.S. Pat. No. 4,907,584, the disclosure of which is incorporated herein by reference. The mask disclosed therein includes a generally annular seal comprised of a peripheral sidewall having an inturned flexible flap seal adjacent a free end thereof, with the inturned seal being configured for confronting sealing engagement with a user's face as above described. Spaced about the peripheral seal wall are plural, upstanding, flexible ribs which serve to support the peripheral wall and an inturned portion of the seal member located generally outward of the face-engaging surface portion of the seal flap. The described seal structure is intended to permit the flap seal and peripheral sidewall to distort without experiencing any mode of seal defeating deformation such as crimping, buckling, folding or other modes of collapse. In this seal structure, the structural support ribs are located and configured in a manner to provide adequate seal flap support where seal deformation is not required (i.e., at the "low" points of the contours of the user's face) and to resiliently deform in a manner to permit easy and uniform distortion of the seal flap in those areas where distortion is necessary to accommodate "high" points on the contours of the user's face.

Other respiratory masks having flexible flap facial seats are disclosed in U.S. Pat. Nos. 4,167,185 and 4,677,977. Masks comprising both continuous cushion and flexible flap sealing features are described in U.S. Pat. Nos. 2,931,356, 3,330,273, and 4,971,051.

Despite its general efficacy in affording a desired seal against the typical user's face, the construction of the inturned flexible flap is such that the contours of certain users' faces may preclude reliable sealing by masks of this type. In this regard, the seal flap includes an opening having an enlarged lower portion to accommodate lower regions of the user's nose (and possibly the user's mouth) and an upwardly extending narrow slot portion adapted to receive the bridge of the nose. The slot bifurcates the flap into a pair of opposed flap portions adapted to lie against opposite sides of the user's nose during use. The front portion of the nose is left uncovered.

U.S. Pat. No. 4,167,185 teaches a flexible flap type mask seal which incorporates reinforcement webs or struts in the nasal flap portions of the seal to force the flap portions against the bridge of the user's nose during use. This arrangement, however, exerts localized pressure on the user's face which, in turn, results in increased user discomfort.

U.S. Pat. No. 4,655,213 describes a nasal mask that substantially surrounds the user's nose and provides a continuous cushion type perimetrical seal therearound. Such perimeter seals are required because the mask seal bodies are over-sized to accommodate, but not contact, the user's nose. The seals provided by these masks are thus conceptually similar to and suffer from essentially the same drawbacks as the continuous cushion type mask seals discussed at the outset.

In order to improve the sealing effects and comfort of the above-described masks, flexible resilient mask flap seals have been developed which may be adapted for attachment to a respiratory mask body or may be removably placeable over the facial seal of an existing respiratory mask. A respiratory mask facial seal of this type is described in U.S. Pat. No. 5,540,223, the disclosure of which is incorporated by reference herein. Further seals of this type are shown in Soft Series Literature from Respironics, Inc. of Pittsburgh, Pa.

It is also known to provide the above-described type masks with forehead spacer or cushioning elements. The above-referenced U.S. Pat. No. 4,907,584 further describes a forehead spacer element for limiting deformation of the mask seal when in engagement with a user's face. In the featured embodiment, the spacer comprises a foam rubber spacer block attached to a pressure sensitive adhesive strip which can be applied to the mask.

Other forehead spacer/cushion elements are shown in U.S. Pat. Nos. 5,243,971, 5,517,986, 5,570,689, and International Publication No. WO 98/04310. However, a disadvantage exists with known forehead spacer/cushion elements in that multiple forehead pad sizes, mechanically complicated or cumbersome adjustment mechanisms, or both are currently required to accommodate various patient physical profiles.

An advantage exists, therefore, for a respiratory mask that affords an effective yet comfortable seal for all users, not withstanding the size or shape of a particular user's face and that does not require multiple forehead pad sizes or mechanical forehead pad adjustment mechanisms.

Respiratory masks usually require an exhaust vent or port for purging the system of $CO_2$ laden air, especially masks intended for use in a single-limb ventilation circuit. A known respiratory mask incorporates ports in the body of the mask. However, several drawbacks have been found to be associated with ports in the body of the mask. For example, air exiting the mask ports may create noise near the user's face, blow on the patient causing discomfort, or blow on the patient's bed partner.

To address these disadvantages, Respironics, Inc. has developed and manufactured a swivel conduit under the name Whisper Swivel® Exhalation Port. This two-piece conduit provides a swivel connection between the mask elbow and the delivery conduit and also includes downwardly directed exhaust slits for directing the $CO_2$ laden exhaust away from the patient.

However, an advantage exists for an exhaust device which provides the ability to rotate, reduces noise and that disposes the exhalation port or ports closer to the mask volume than is currently possible using the Whisper Swivel device.

SUMMARY OF THE INVENTION

The present invention provides an improved respiratory mask that reliably and comfortably seals facial contours. According to the presently preferred embodiment, the respiratory mask of the present invention includes a thin sealing area. This thin section permits the mask to more easily adapt to the contour of the human face and seal at low pressures with minimal facial pressure.

According to another aspect of the present invention, the respiratory mask is provided with a gel forehead cushion/spacer element. As the gel material is more compliant than the foam material used in known forehead cushion. The gel forehead pad is able to accommodate a wider range of physical profiles with increased comfort, and does so without the need to provide for adjustment of the forehead cushion to suit each particular patient.

In yet a further aspect of the present invention, the respiratory mask is provided with a respiratory tubing elbow coupling providing the ability to rotate 360 degrees about the faceplate of the respiratory mask and having an integrated tapered exhaust port and a polycarbonate leak ring for exhausting exhaled gases from the respiratory mask. The positioning of the exhaust ports closer to the respiratory mask body provides a more efficient exhausting of gases, and the design of the exhaust ports reduces the noise level created by the flow of air through typical fixed orifice.

These and other advantages, objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

Figure 1A:
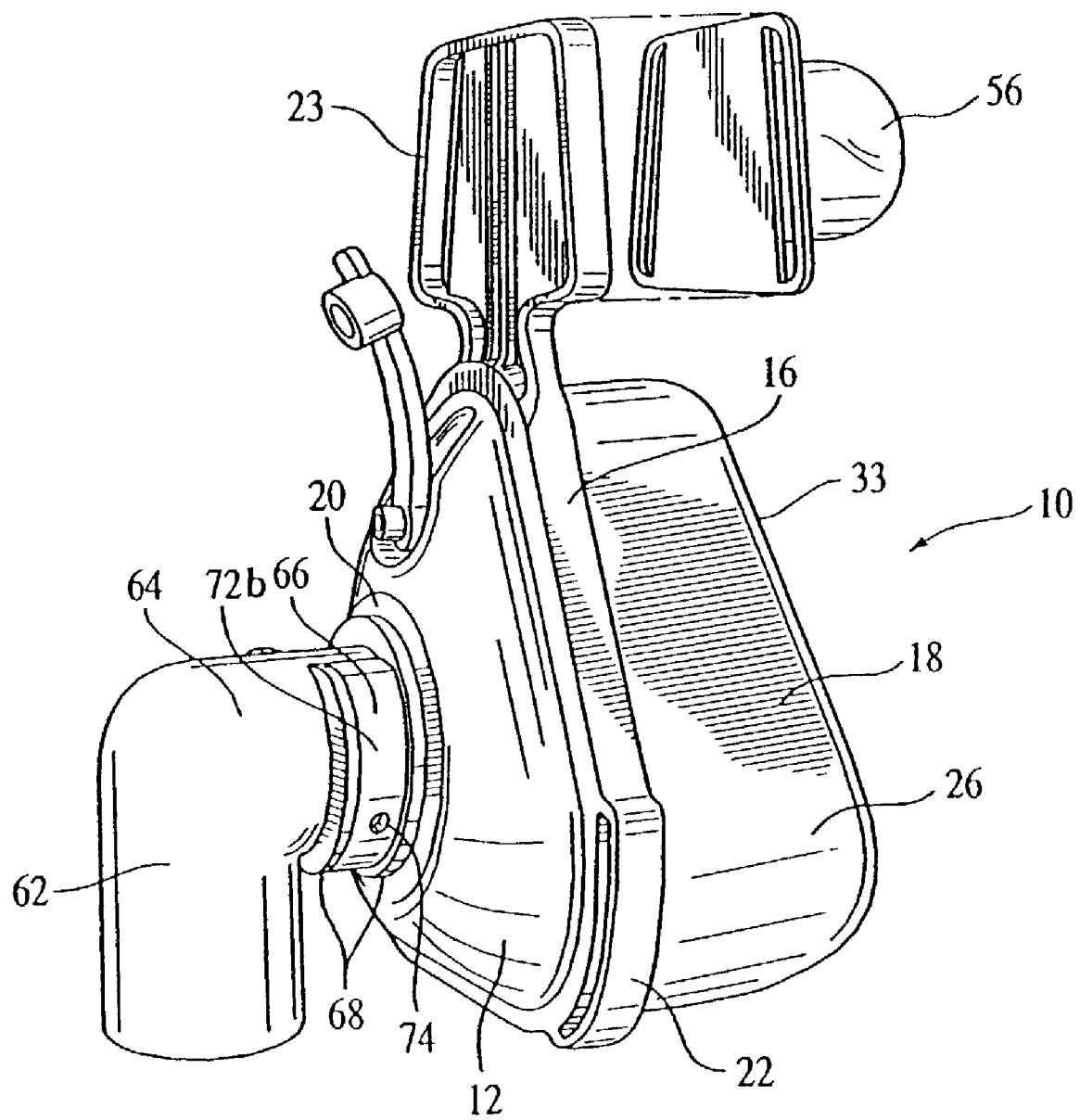
FIGS. 1A and 1B are front and rear perspective views, respectively, of a first embodiment of a respiratory mask according to the principles of the present invention.

DETAILED DESCRIPTION OF THE PRESENTLY PREFERRED EXEMPLARY EMBODIMENTS OF THE INVENTION

There is generally indicated at 10 in FIGS. 1A, 1B and 3-6 a respiratory mask constructed according to one preferred embodiment of the present invention. Respiratory mask 10 includes a shell or body portion 12, which is preferably, but not necessarily, a general rigid, formed structural shell having an open side 14 that defines an annular flange portion 16 to which a flexible, resilient, unitary seal member 18 is affixed by the provision of a retainer ring 19.

Shell 12 also defines an opening 20 or other suitable means for connecting mask 10 to a supply of gas for administration to a patient on another side of the shell opposite open side 14. The mask shown is a nasal or half mask. It is to be understood, however, that the invention contemplates a full face mask covering both the nasal and oral openings of the patient. Shell 12 further includes two outwardly projecting strap retaining tabs 22 and an upwardly projecting strap retaining tab 23, each having suitable elongated apertures 24 that receive and retain suitable conventional head straps (not shown) for retaining the mask 10 with respect to the face of a patient.

Figure 6:
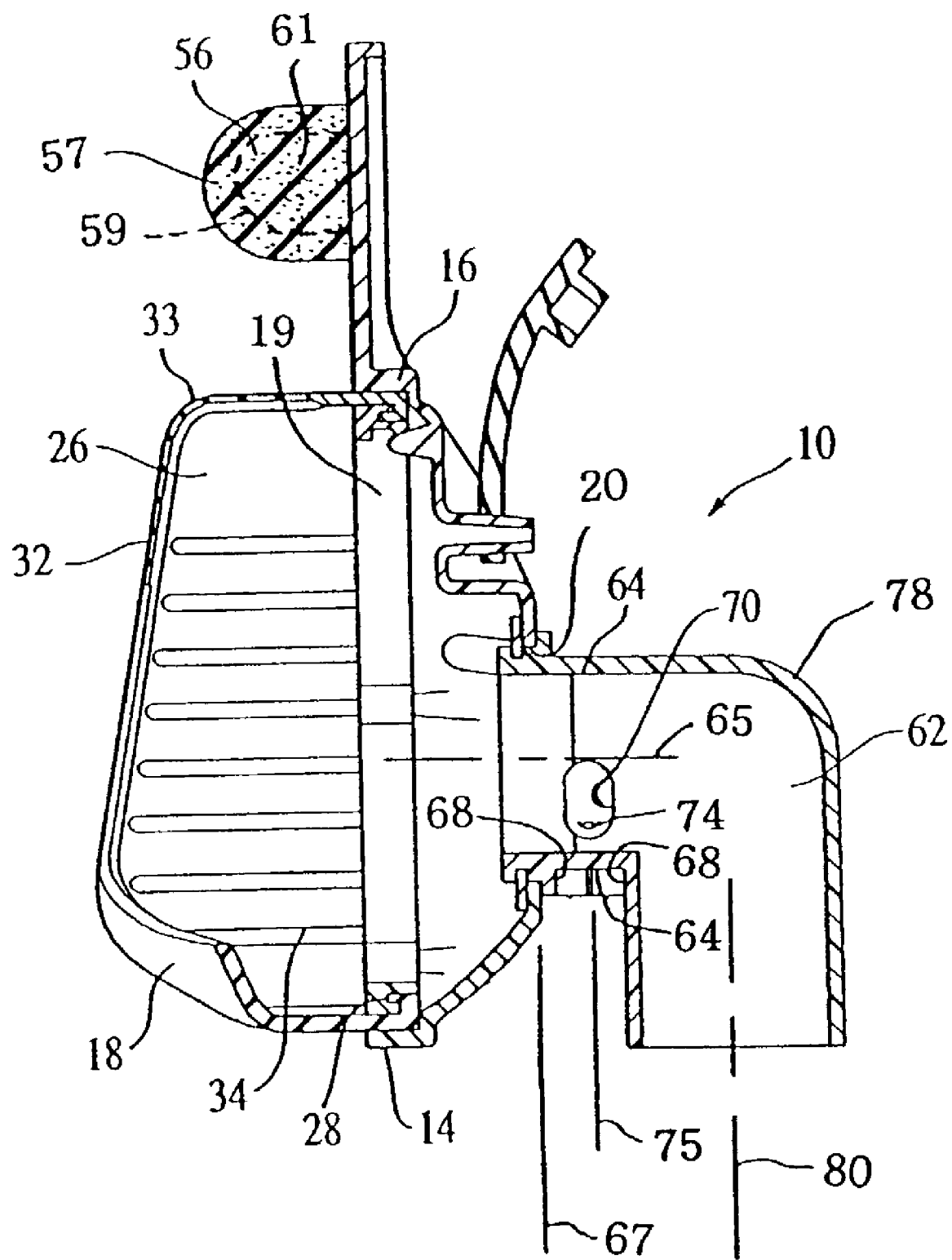
FIG. 6 is a cross-sectional view of the respiratory mask taken along line 6-6 of FIG. 4.

Seal 18 includes a solid flexible peripheral wall portion 26, as shown in FIG. 6, having an annular base or inner end 28 that is fixedly and sealingly retained with respect to flange 16 and an outer end 33. Peripheral wall portion 26 has a first thickness between inner end 28 and outer end 33. Adjacent outer end 33 of peripheral wall portion 26 is a generally annular inturned surface 32 spaced from the mask shell 12 for confronting engagement with a patient's face. Annular surface 32 projects inwardly of peripheral wall portion 26 from a first juncture, which corresponds to outer end 33 of peripheral wall portion 26. In addition, annular surface 32 is generally triangular in shape having an upper apex angle 32A and two lower angles 32B. Annular surface 32 is provided with a first sealing portion 31 and a thin sealing portion 35, as perhaps best shown in FIG. 7.

First sealing portion 31 begins at the first juncture, i.e., outer end 33 of peripheral wall portion 26, and extends inwardly. First sealing portion 31 has a second thickness that is substantially the same as the first thickness of peripheral wall portion 26. Thin sealing portion 35 begins interiorly of the juncture between peripheral wall portion 26 and first sealing portion 31 of annular surface 32 and extends to an inner edge 36 defining an opening 38. More specifically, thin sealing portion 35 begins at a second juncture 37 located interiorly of the first juncture that generally corresponds to the termination point of first sealing portion 31. Thin sealing portion 35 extends from second junction 37 to inner edge 36 defining opening 38. Thin sealing portion 35 has a third thickness that is significantly less than the second thickness of first sealing portion 31. In addition, thin sealing portion 35 lies substantially in a single plane and includes a lower boundary substantially near two lower angles 32B and an upper boundary substantially near upper apex angle 32A.

Figure 7:
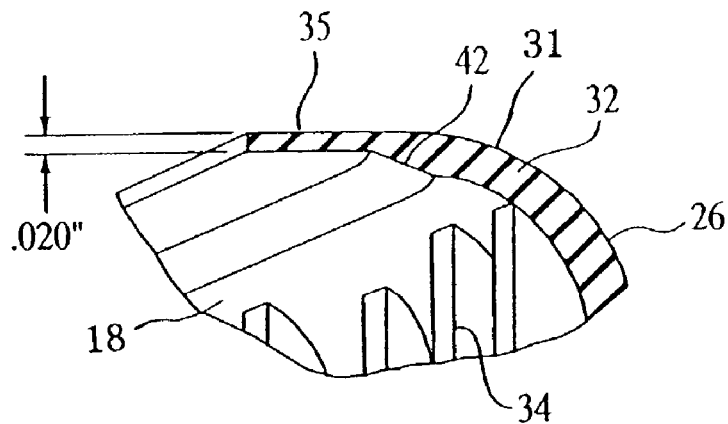
FIG. 7 is a cross-sectional detail view of a mask seal taken along line 7-7 of FIG. 4.

Preferably, seal member 18 further includes a thin bridge portion 40 for confronting engagement with the bridge of a user's nose where a common pressure point occurs in existing masks. Thin bridge portion 40 extends substantially perpendicularly from the upper boundary of the sealing portion 18 to form an upper extension of thin sealing portion 35. Thin sealing portion 35 and the thin bridge 40 are of a uniform thickness of approximately 0.02 inches. A transition area 42, as best shown in FIG. 7, of gradually increased thickness is disposed between thin sealing area 35 and the thicker first sealing portion 31 of the annular surface 32. Transition area 42 also corresponds to second junction 37. For thin bridge portion 40, the transition area 42 extends between peripheral wall portion 26 and thin bridge portion 40.

In the illustrated exemplary embodiment, outer end 33 of peripheral wall portion 26 and annular surface 32 are contoured to accommodate the side of the patient's nose and upper lip. However, for a full face mask, annular surface 32 would additionally be contoured to accommodate the user's cheek and chin structure, and contiguous intervening zones. In either case, variation in user facial structure, especially in the area of the bridge of the nose, and in the chin-to-cheek proportions, makes seal flexibility necessary to accommodate the many different facial contours likely to be encountered. Alternatively, thin sealing portion 35 may also be provided in the lower portion of mask 10 between two lower angles 32B.

Figure 1B:
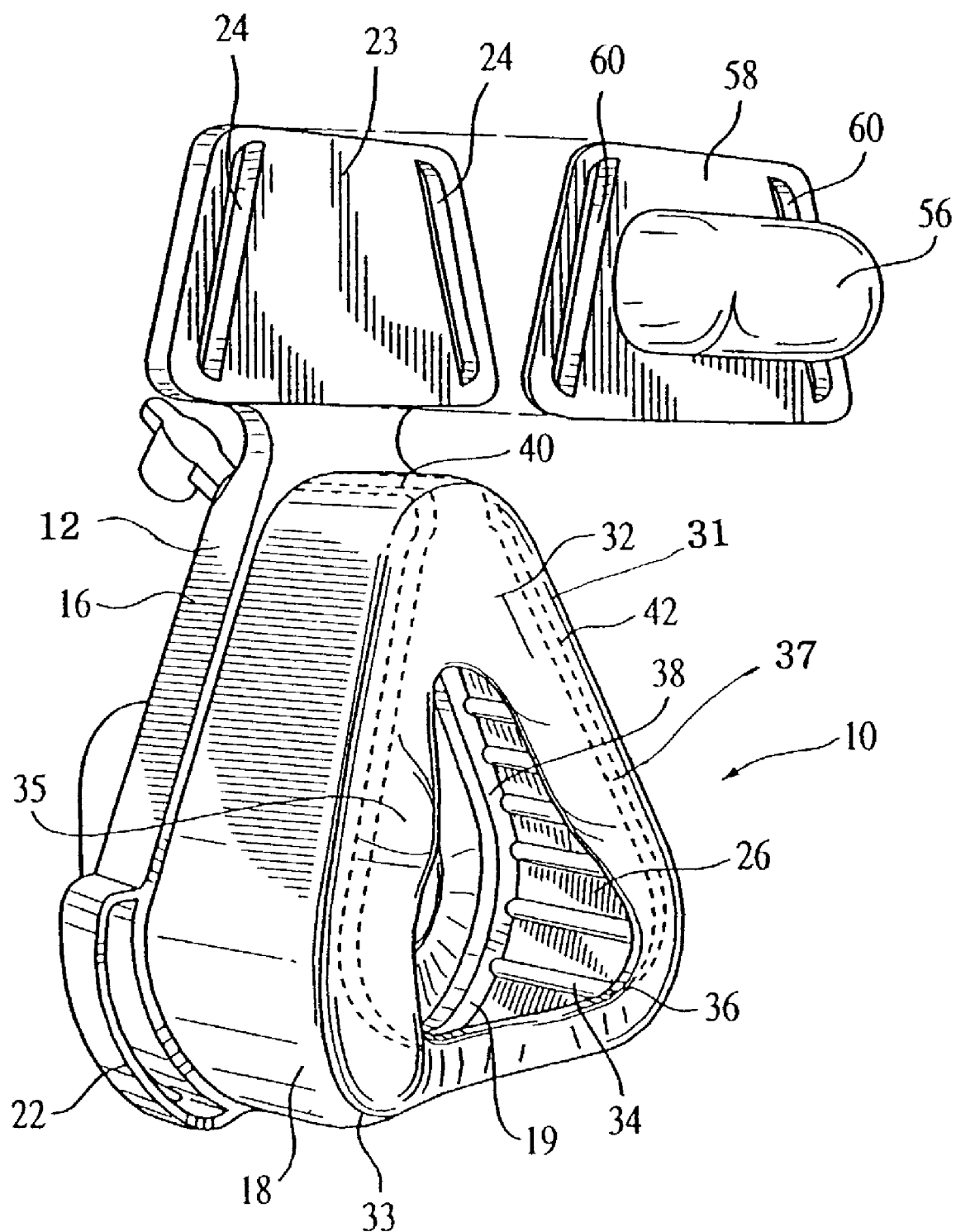
Figure 2:
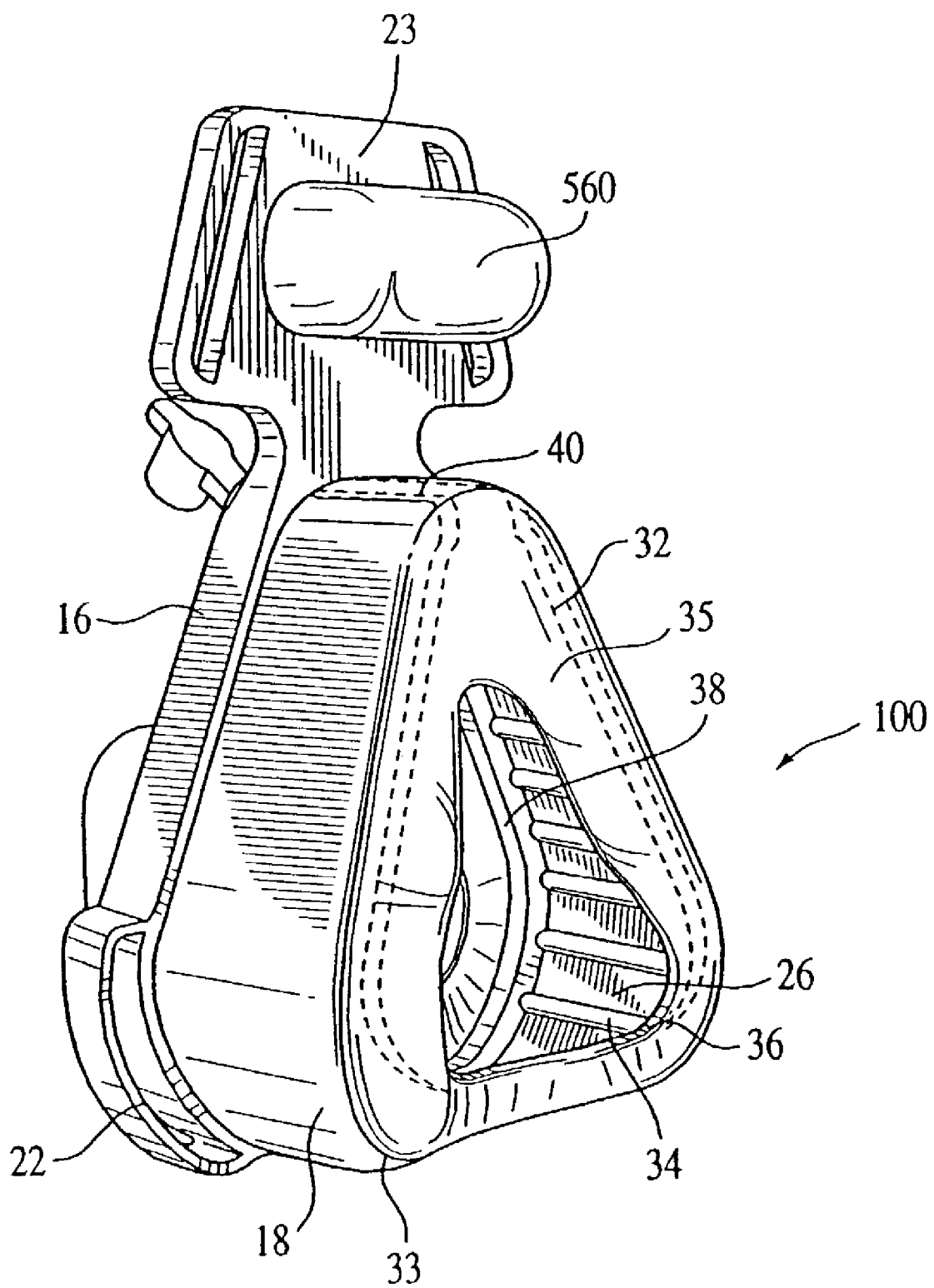
FIG. 2 is a rear perspective view of a second embodiment of a respiratory mask according to the principles of the present invention.
Figure 3:
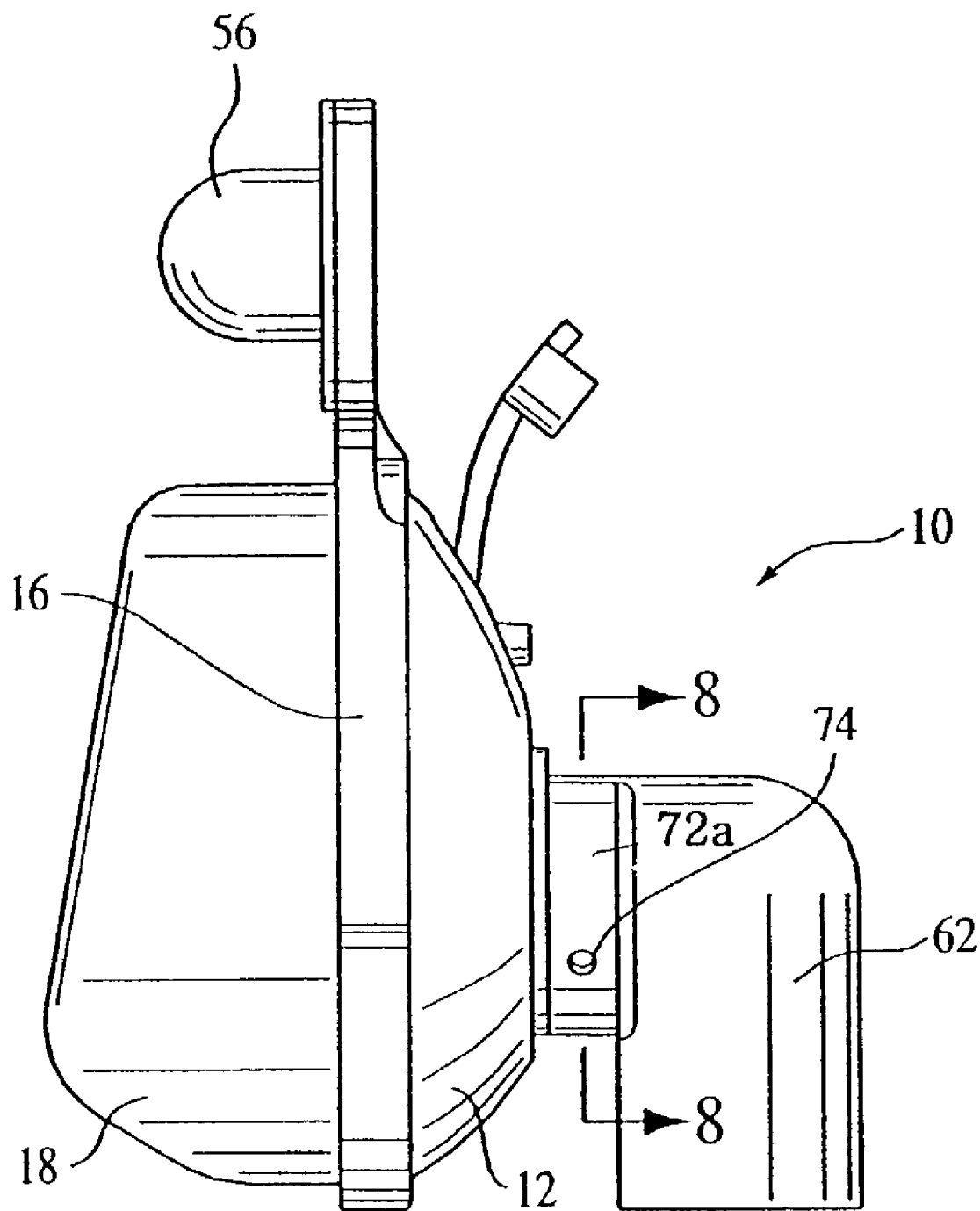
FIG. 3 is a side view of the respiratory mask of FIGS. 1A and 1B.
Figure 4:
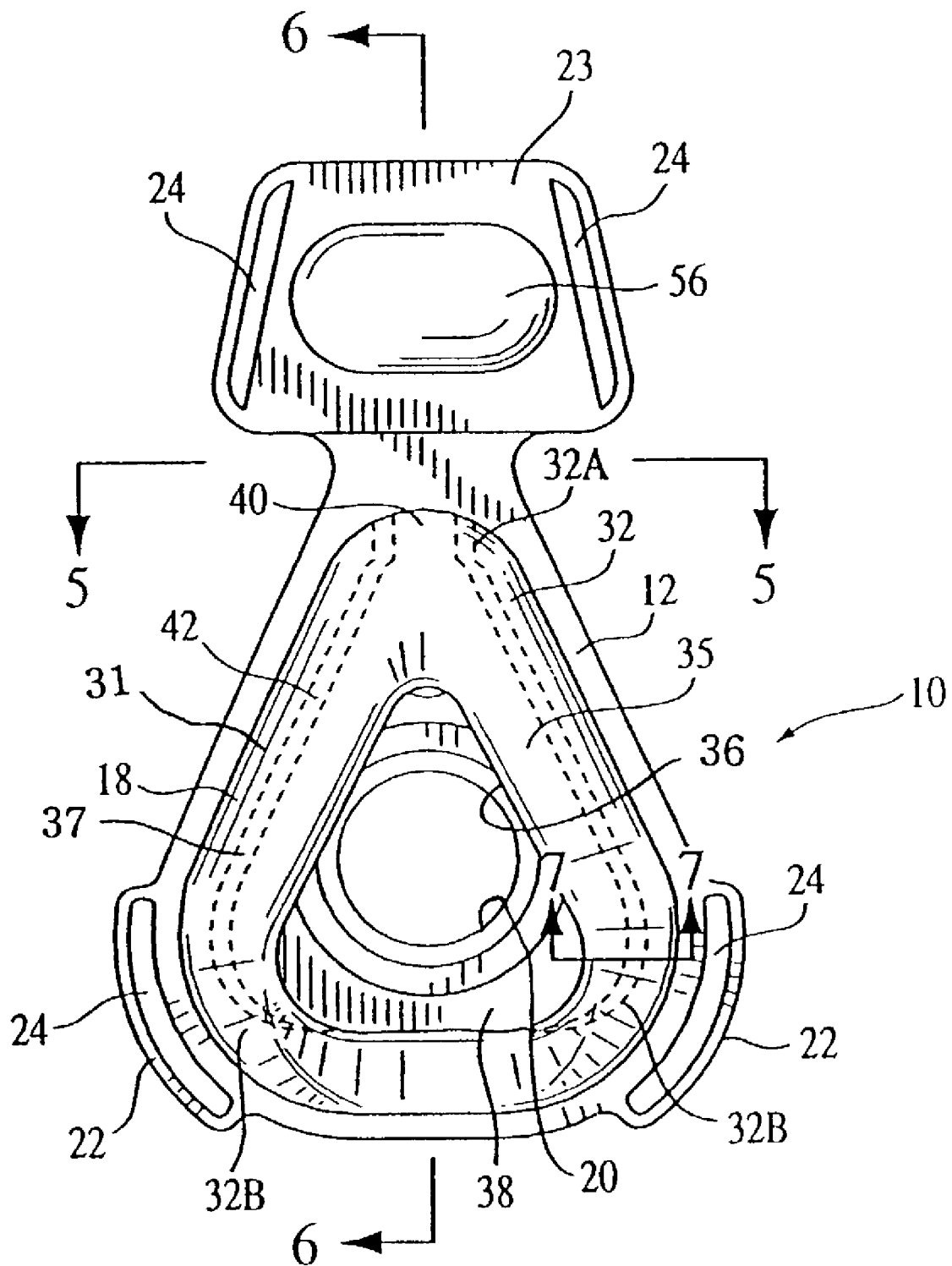
FIG. 4 is a rear view of the respiratory mask of FIGS. 1A and 1B.
Figure 5:
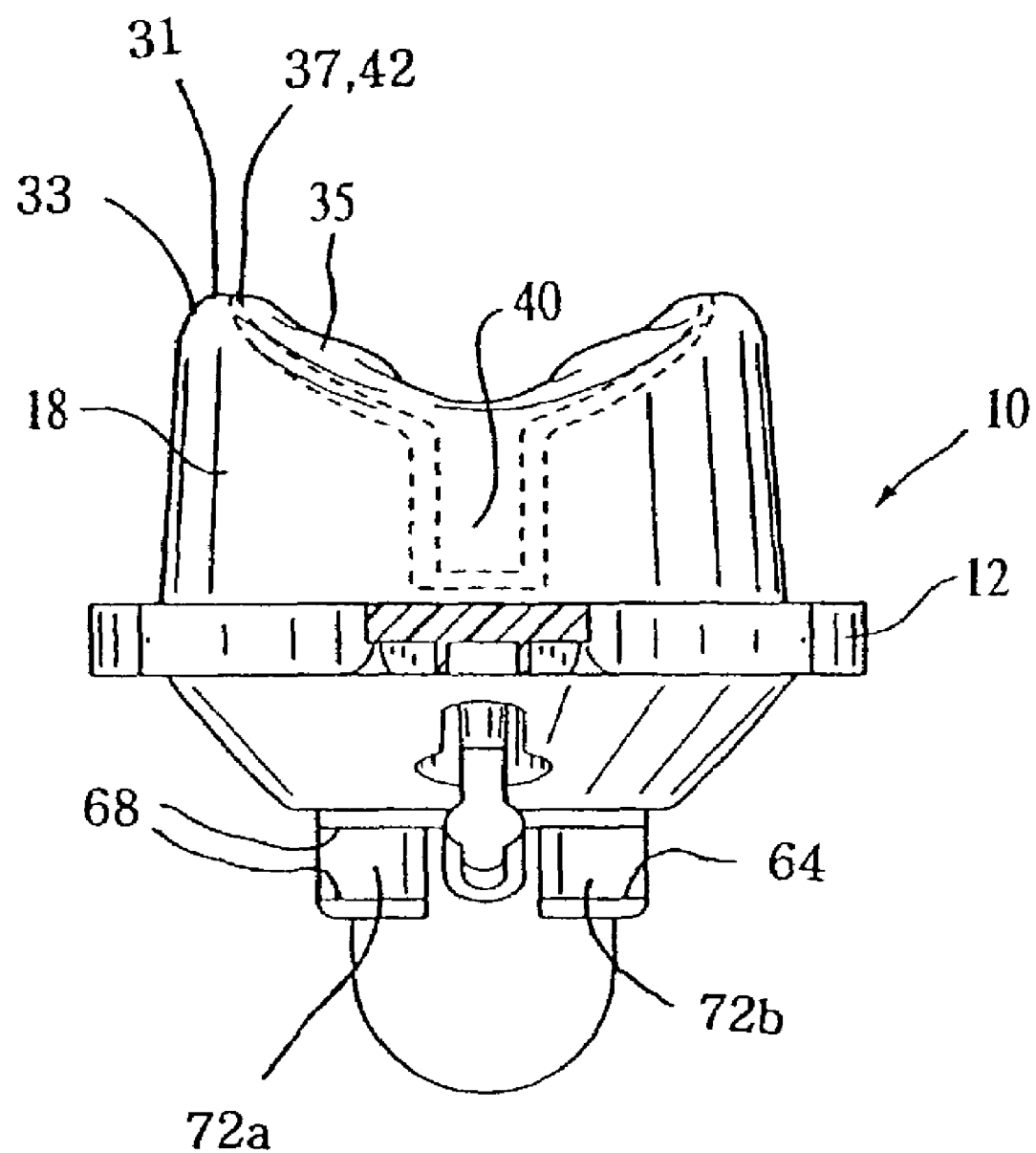
FIG. 5 is a cross-sectional view of the respiratory mask taken along line 5-5 of FIG. 4.

Also shown in FIGS. 1B, 2 and 6, seal member 18 is preferably provided with a plurality of upstanding flexible members or ribs 34, which are spaced circumferentially about and integral with the interior periphery of peripheral wall portion 26. Ribs 34 project radially inwardly of wall portion 26 and their length extends intermediate inner end 28 and outer end 33. Ribs 34 resiliently support the peripheral wall portion 26 and the annular surface 32 against excessive deformation.

A further aspect of the presently preferred embodiment of the present invention pertains to the provision of a spacer element or forehead cushion 56, which is, but not necessarily, removably or fixably attached to upwardly projecting strap retaining tab 23. It should be understood that when mask 10 is donned by a patient, retaining tab 23 overlies the patient's forehead. With reference to FIG. 1B, there is shown a forehead cushion 56 in the form of a generally oval body.

FIGS. 1, 1B and 3-6 illustrate the preferred embodiment in which the forehead cushion 56 is attached to a removable base plate 58 having at least one elongated aperture 60 and preferably two elongated apertures 60. Retaining straps (not shown) pass through both elongated apertures 60, 24 of the removable base plate 58 and the upwardly projecting strap retaining tab 23 to securely, yet removably attach forehead cushion 56 to strap retaining tab 23.

Forehead cushion 56 is formed of a resilient gel substance i.e., a urethane gel, such as a viscoelastic polyurethane polymer, possessing resilience or recoil characteristics corresponding substantially to those of human fat tissue. More specifically, forehead cushion 56 preferably has a resiliency as defined by durometer measured on the Shore 00 scale, which is used to gauge the resiliency of very soft resilient materials, of about 10 or softer and, most preferably, about 0. Such resiliency corresponds substantially to that of human fat tissue, which also exhibits a durometer reading of 0 on a Shore 00 scale. While virtually indistinguishable from human fat tissue when measured on the Shore 00 scale, the gel substance of forehead cushion 56 preferably exhibits a resiliency or durometer on the Shore 000 scale, which is a scale used to measure extremely soft resilient materials, of from about 20 to 45. By comparison, human fat tissue registers a durometer of about 10 on the Shore 000 scale. A suitable gel substance is disclosed, for example, in U.S. Pat. Nos. 5,647,357 and 5,884,624. Although the gel substance is described in these patents with respect to the seal portion of a respiratory mask, the present invention contemplates using the same substance for forehead cushion 56.

In one embodiment of the present invention, forehead cushion 56 is covered by a protective covering. The covering increases the durability of the forehead cushion while also permitting easy cleaning of the cushion. The covering must satisfy several physical criteria. It must, inter alia: (1) resist tearing and puncturing, (2) tightly conform to the forehead cushion without changing or deforming the contours thereof, (3) be chemically compatible with the cushion, (4) be biocompatible and non-irritating to a user's skin, and (5) be sufficiently thin and supple such that its presence has a negligible impact on the resultant durometer of forehead cushion 56. In this regard, an exemplary embodiment of the present invention contemplates that the covering comprise a thin (approximately 2 to 10 mils thick) flexible plastic film. Urethane has been found to be preferable for this particular purpose as such material meets not only the objectives of the present invention but is also comparatively inexpensive and easy to apply to the surface of forehead cushion 56.

The covering may be applied to forehead cushion 56 by any suitable process. For instance, liquid urethane may be applied by spraying or dipping and then permitted to cure. Preferably, however, the urethane is prefabricated by vacuum forming so as to produce a skin of controllable and uniform thickness that is subsequently vacuum formed to the forehead cushion using conventional techniques.

As yet another alternative embodiment, the present invention contemplates that forehead cushion 56 be defined by substances of increasingly softer durometers in a direction toward the surface of the cushion that contacts the patient, such that the softest materials, comprising the previously discussed gel substance and possessing the resiliency characteristics described hereinabove, constitute the face-contacting portion of the forehead cushion 56.

In further embodiment of the present invention, as shown in FIG. 6, forehead cushion 56 includes a first portion 57 defined by the gel substance discussed above and a second portion 61 defined by a selectively formable substance so that the general shape of forehead cushion 56 can be customized to enable the forehead cushion to conform comfortably on the surface of the patient.

The selectively formable substance in second portion 61 of forehead cushion 56 is capable of being placed in a malleable state so that it molds from a first pattern into a second pattern. The formable substance is also capable of being placed in a fixed state so that it retains the second pattern after being so molded. Dashed line 59 in FIG. 6 represents the interface between first portion 57 and second portion 61 when second portion 61 is in its original, first pattern, i.e., prior to being molded to match the contours of the patient.

In an exemplary embodiment of the present invention, the formable substance in second portion 61 of forehead cushion 56 is heat activated so that it transitions from the fixed state to the malleable state upon being heated to a certain level. It also transitions from the malleable state to the fixed state upon being cooled to certain level. In one embodiment of the present invention, the formable substance defining second portion 61 is a combination of the above-described gel substance and a stiffening agent, such as ethyl vinyl acetate. Although a range of mixture ratios are possible to achieve a variety of stiffnesses for second portion 61, in a preferred embodiment of the present invention, the second portion is a uniform mixture of approximately 60% gel substance and 40% stiffening agent.

This embodiment of the present invention provides a customizable forehead cushion 56 for contacting the respiratory mask in a comfortable fashion. More specifically, by providing a formable substance as second portion 61 of forehead cushion 56, the forehead cushion can be macro-customized to match the general contours of the forehead of the patient, such as the bone structure underlying the portions of the patient's face over which strap retaining tab 23 is to be placed. In addition, first portion 57 of forehead cushion 56, being a gel substance as described above, provides the beneficial effects of micro-customization in that the gel readily conforms to the external features of the patient's face and without being patterned to match the specific features of the user. Instead, the consistency of the gel allows the first portion to fill in the gaps on the surface of the user once the forehead cushion is applied to the user. Thus, a single forehead cushion 56 provides the benefits of micro-customization and macro-customization.

Furthermore, the formable substance in second portion 61 can be reshaped, as needed, merely by causing the formable substance to transition again to the malleable state, which, in the above embodiment, is accomplished by reheating the second portion. Thus, forehead cushion 56 can be re-customized if, for example, the patient is unsatisfied with a previous attempt to customize the forehead cushion. Still further, because the gel substance of first portion 57 provides the beneficial effects of micro-customization and because the second portion can be customized to match the general contours of a patient, a commonly configured forehead cushion 56 having first and second portions 57 and 61 can be adapted for use with a wide variety of patients, thereby maximizing the efficiency of the manufacturing process. This feature also makes it possible to minimize the number of different off-the-shelf variations in the forehead cushion in order to provide a comfortable forehead pad suitable for each patient from a group of patients having a wide range of different physical characteristics. In addition, no special mechanisms for adjusting the forehead pad are need in order to allow a commonly configured mask to be used with a wide variety of patients.

In the embodiment of forehead cushion 56 illustrated in FIG. 6, first portion 57 and second portion 61 are generally integral with one another with the junction between the two portions being defined by a interface 59. It is to be understood, however, that the interface between first portion 57 and second portion 61 need not be as shown. On the contrary, the interface between first portion 57 and second portion 61 can vary in three dimensions depending on the desired structural characteristics of the forehead cushion.

Although FIG. 6 illustrates a relatively distinct separation between first portion 57 and second portion 61, it is to be understood, however, that there need not be such a distinct separation of these portions. On the contrary, forehead cushion 56 can be constructed and arranged so that the mixture ratio of gel to stiffening agent gradually changes. For example, in one embodiment of the present invention, the mixture ratio of gel to stiffening agent gradually increases in the direction toward the surface of the forehead cushion 56 that contacts the patient, which is substantially 100% gel substance, with no specifically defined transition from second portion 61 to first portion 57. The present invention also contemplates that the mixture ratio can vary in three dimensions. Also, the rate of change in the mixture ratio from one portion to another in forehead cushion 56 need not be constant, i.e., linear. Instead, the rate of change in mixture ratios can vary depending on the desired characteristics for forehead cushion 56. Furthermore, the physical location of the areas of changing mixture ratios in the seal can vary depending on the needs of the user. Also, the present invention contemplates that there may be multiple layers of first portion 57 or second portion 61 or both defining forehead cushion 56.

In an alternative embodiment of a respiratory mask 100 according to the principles of the present invention, as illustrated in FIG. 2, a gel cushion 560, which is otherwise the same as gel cushion 56 discussed above, is fixedly attached directly to strap retaining tab 23 of mask 100 without the use of base plate 58. Although gel cushion 56 and 560 are illustrated as being generally oval shaped, it is to be understood that the present invention contemplates other suitable shapes, such as trapezoidal or rectangular, for the gel cushion. Strap retaining tab 23 is preferably trapezoidal in shape with elongated apertures 24 at slight angles to provide a comfortable yet secure retaining strap arrangement.

Figures 9A, 9B:
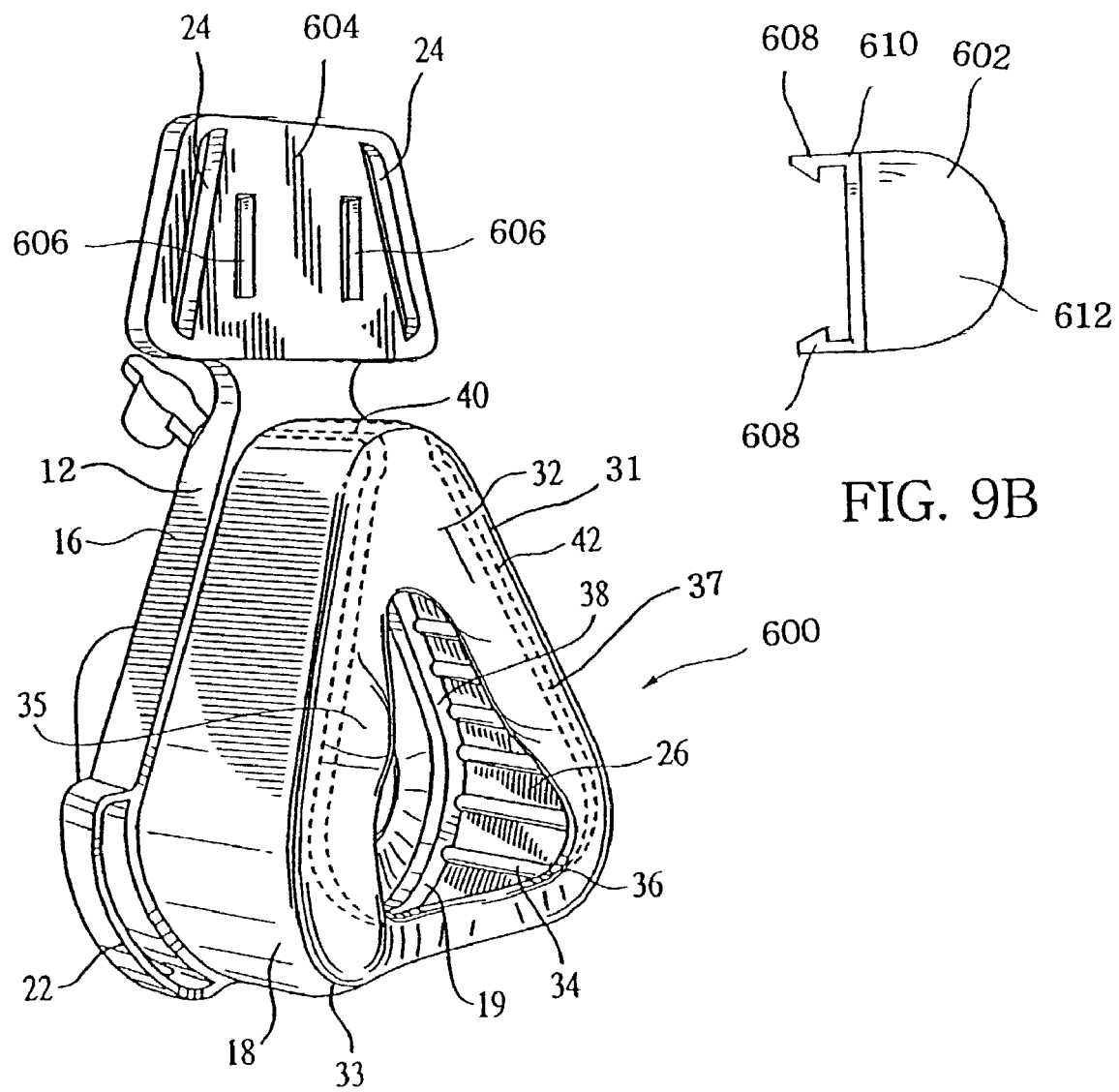
FIGS. 9A and 9B are perspective view of a respiratory mask and a side view of a forehead pad, respectively, according to a third embodiment of the present invention.

Yet another alternative embodiment of the present invention, a respiratory mask 600 and forehead cushion 602 according to the principles of the present invention is illustrated in FIGS. 9A and 9B. Forehead cushion 602 is that a gel cushion that is otherwise the same as gel cushion 56 discussed above except that it is removeably attached to strap retaining tab 604 of mask 600 without the use of base plate 58. In the illustrated exemplary embodiment, removeable coupling of the forehead cushion to the strap retaining tab is accomplished via a snap-fit engagement of the forehead cushion to the strap retaining tab. More specifically, a pair of snap-fit slots 606 are provided in strap retaining tab 604 that receive protrusions 608 that extend from one side of a snap-fit plate 610. Gel substance 612 is fixed to the other side of snap-fit plate 610, for example, by adhesive attachment. Of course, the present invention contemplates that the snap-fit slots and protrusions can be provided in any manner on the strap retaining tab 604 and snap-fit plate 610.

It is to be understood that the present invention contemplates using other mechanisms to releaseably secure the gel forehead pad to the strap retaining tab. For example, a hook and loop attachment mechanism, such as VELCRO®, or a tongue and groove attachment mechanism can be used to releaseably secure the forehead pad to the strap retaining tab.

Yet a further aspect of the presently preferred embodiment involves an elbow coupling 62 rotatably attached at a first end portion 64 to opening 20 in shell 12 for coupling mask 10 to a supply circuit operatively connected to the supply of gas e.g., a blower or other suitable means for providing a flow of pressurized breathing gas. The rotatable swivel attachment of the first end portion 64 of the elbow coupling 62 provides the supply circuit with the ability to rotate 360° about the mask 10. In the illustrated embodiment, first end portion 64 of coupling 62 extends from mask shell 12 along a first axis 65 generally perpendicular to a first plane 67 defined by the side of respiratory mask shell 12 opposite open side 14. First plane 67 generally corresponds to the plane in which opening 20 lies.

Figure 8:
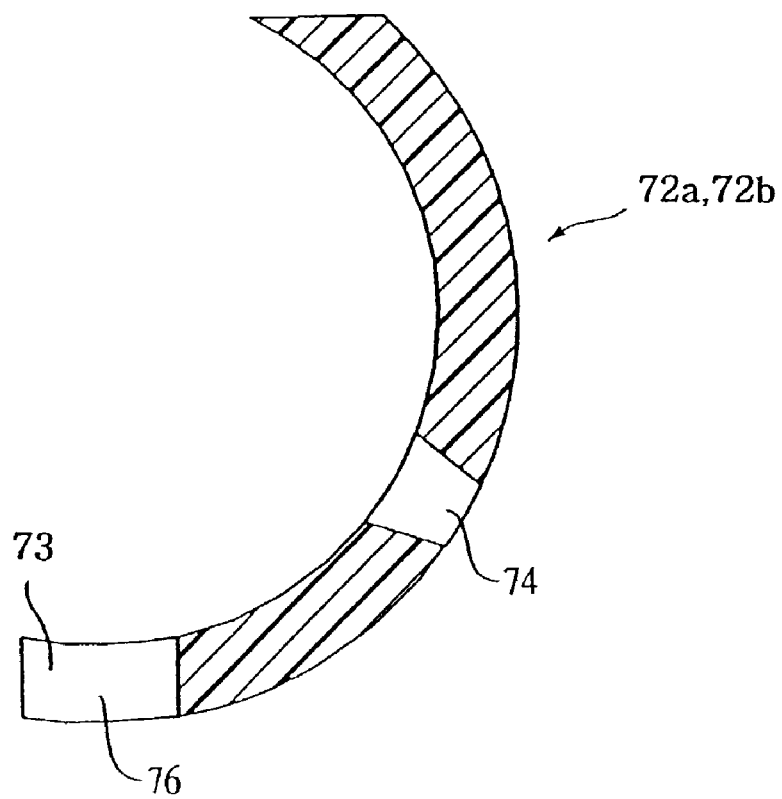
FIG. 8 is a cross-sectional detail view of a single arc section taken along line 8-8 of FIG. 3.

In addition, the elbow coupling 62 includes integral exhaust ports defined in first end portion 64 for purging exhaled gas from the respiratory mask system. First end portion 64 preferably includes a slot 66 with side walls 68 and at least one, and preferably two, openings 70 located 120° left and right from the vertical centerline of elbow coupling 62. At least one, and preferably two, arc sections 72a and 72b are positioned within slot 66 on first end portion 64. An exemplary embodiment of an arc section 72a, 72b is shown in FIG. 8. As shown in this figure, each arc section includes a tapered through hole 74 overlying one of the two openings 70. Tapered through hole 74 is larger on the inside diameter and smaller on the outside diameter to provide a quiet passage of gas through the holes.

Arc sections 72a and 72b are preferably formed of a non-elastomeric polycarbonate material, but may be formed of any suitable material including elastomeric materials. Arc sections 72a and 72b have lower ends 73 having a cut out portion 76 such that arc sections 72a and 72b matingly join about the circumference of first end portion 64 of coupling 62. Arc sections 72a and 72b are preferably glued into slot 64 in elbow coupling 62.

Opening 70 and through hole 74 together define an exhaust port that is disposed near shell 12 to minimize dead space in the respiratory circuit. In addition, the exhaust port defined by opening 70 and through hole 74 are configured and arranged to exhaust gas from the first end portion of the coupling in a second plane 75 that is generally parallel to first plane 67. By directing exhaust gases in this manner, the present invention prevents that exhaust gas from disturbing the patient or the patient's bed partner. Arc sections 72a and 72b make it possible to easily manufacture tapered exhaust ports in the coupling while providing opening 70 and through hole 74 in the locations shown maximized comfort associated with the exhausting of gas from the respiratory mask system.

Coupling 62 includes an elbow portion 78 operatively coupled to first end portion 64. Elbow portion 78 includes a second axis coaxially aligned with the first axis 65 and a second axis 80 generally parallel to first plane 67 and second plane 75 so that coupling 62 defines a 90° bend in the patient circuit. It is to be understood, however, that the elbow portion of coupling 62 can be defined over a range of angles other than the 90° angle shown in the figures.

Although the invention has been described in detail for the purpose of illustration based on what is currently considered to be the most practical and preferred embodiments, it is to be understood that such detail is solely for that purpose and that the invention is not limited to the disclosed embodiments, but on the contrary, is intended to cover modifications and equivalent arrangements that are within the spirit an scope of the appended claims.

What is claimed is:

1. A patient interface assembly comprising:
   a respiratory mask shell having a first portion adapted to overlie a bridge of a nose of a user responsive to the interface assembly being donned by a patient;
   a tab operatively coupled to the respiratory mask shell generally at the first portion and extending therefrom such that at least a portion of the tab overlies a patient's forehead responsive to the interface assembly being donned by such a patient, and wherein the tab is operatively coupled to the mask shell such that the tab remains in a fixed position relative to the mask shell responsive to such a patient wearing the patient interface assembly;
   a base adapted to be removeably attachable to the tab; and
   a cushion disposed on the base, wherein the tab is configured such that a position of the cushion is fixed relative to the respiratory mask shell responsive to the base being attached to the tab.

2. The interface assembly of claim 1, wherein the cushion is formed from a gel substance having a Shore 00 durometer of less than about 10.

3. The interface assembly of claim 1, wherein the cushion is formed from a gel substance having a Shore 000 durometer from about 20 to about 45.

4. The interface assembly of claim 1, wherein the base further includes a first elongated aperture defined therein.

5. The interface assembly of claim 4, wherein the base further includes a second elongated aperture defined therein, wherein the first and the second elongated apertures are defined in first and second portions of the base, respectively, and wherein the first and the second portions are located on opposite sides of the cushion attached to the base.

6. The interface assembly of claim 5, wherein the first elongated aperture extends generally parallel to an edge of the base proximate to the first portion, and wherein the second extends generally parallel to an edge of the base proximate to the second portion.

7. The interface assembly of claim 4, further comprising a headgear strap positioned within the first elongated aperture.

8. The interface assembly of claim 1, wherein the tab includes a first elongated slot defined in a first portion of the tab and a second elongated slot defined in a second portion of the tab, wherein the base includes a third elongated slot defined in a first portion of the base and a fourth elongated slot defined in a second portion of the base, and wherein the first and the third elongated slots align with one another and the second and fourth elongated slots align with one another responsive to the base being positioned on the tab.

9. The interface assembly of claim 8, further comprising:
   a first headgear strap portion positioned in the first and the third elongated slots;
   a second headgear strap positioned in the second and the fourth elongated slots.

10. The interface assembly of claim 1, wherein the resilient cushion includes a portion defined by a selectively formable substance that is adapted to be molded from a first pattern into a second pattern and to retain the second pattern responsive to being so molded.

11. The interface assembly of claim 10, wherein the selectively formable substance includes a combination of the gel substance and a stiffening agent.

12. The interface assembly of claim 11, wherein the combination of the gel substance and the stiffening agent is a uniform mixture of approximately 60% gel substance and 40% stiffening agent.

13. The interface assembly of claim 12, wherein a mixture ratio of the gel substance to stiffening agent gradually changes over a dimension of the resilient cushion.

14. The interface assembly of claim 1, further comprising:
   a first headgear attachment element provided on a first side of the tab; and
   a second headgear attachment element provided on a second side of the tab.

15. The interface assembly of claim 14, wherein the first headgear attachment element includes a first elongated slot defined in a first portion of the tab and the second headgear attachment element includes a second elongated slot defined in a second portion of the tab.

16. The interface assembly of claim 1, wherein the cushion is selectively attachable to the base or wherein the cushion is permanently coupled to the base.

17. The interface assembly of claim 1, wherein the tab includes:
   a head portion having a first width; and
   a neck portion having a second width that is less than the first width, and wherein the first headgear attachment element the second headgear attachment element are provided on opposite sides of the head portion.

18. A patient interface assembly comprising:
   a respiratory mask shell having a first portion adapted to overlie a bridge of a nose of a user responsive to the interface assembly being donned by a patient;
   a tab coupled to the respiratory mask shell at the first portion and extending therefrom such that the tab overlies a patient's forehead responsive to the interface assembly being donned by such a patient, wherein the tab includes a first elongated slot defined in a first portion of the tab and a second elongated slot defined in a second portion of the tab;
   a base adapted to be removeably attachable to the tab, wherein the base includes a third elongated slot defined in a first portion of the base and a fourth elongated slot defined in a second portion of the base, and wherein the first and the third elongated slots align with one another and the second and fourth elongated slots align with one another responsive to the base being positioned on the tab; and
   a cushion disposed on the base.

19. The interface assembly of claim 18, further comprising:
   a first headgear strap portion positioned in the first and the third elongated slots; and
   a second headgear strap portion positioned in the second and the fourth elongated slots.

* * * * *